United States Patent [19]

Reinhardt et al.

[11] Patent Number: 4,957,787
[45] Date of Patent: Sep. 18, 1990

[54] ARTIFICIAL FLOWER

[75] Inventors: Linda P. Reinhardt, Clinton, Ohio; W. Brent Burleson, Pittsburgh, Pa.

[73] Assignee: PPG Industries, Inc., Pittsburgh, Pa.

[21] Appl. No.: 250,015

[22] Filed: Sep. 27, 1988

Related U.S. Application Data

[63] Continuation-in-part of Ser. No. 110,147, Oct. 19, 1987, abandoned.

[51] Int. Cl.$^5$ .............................. A41G 1/00; B32B 3/26
[52] U.S. Cl. ........................................ 428/24; 428/26; 428/207; 428/905; 428/910
[58] Field of Search ...................... 428/24, 25, 26, 905, 428/207, 910; 521/62

[56] References Cited

U.S. PATENT DOCUMENTS

| | | | |
|---|---|---|---|
| 2,823,421 | 2/1958 | Scarlett | 264/216 |
| 2,940,830 | 6/1960 | Thornhill | 423/339 |
| 3,137,610 | 6/1964 | Flynn | 428/26 |
| 3,351,495 | 11/1967 | Larson et al. | 429/254 X |
| 3,775,227 | 11/1973 | Wilbert et al. | 428/26 X |
| 4,600,146 | 7/1986 | Ohno | 428/26 X |
| 4,681,750 | 7/1987 | Johnson et al. | 429/254 X |
| 4,734,229 | 3/1988 | Johnson et al. | 264/175 X |
| 4,833,172 | 5/1989 | Schwarz et al. | 521/62 |
| 4,861,644 | 8/1989 | Young et al. | 428/195 |

FOREIGN PATENT DOCUMENTS

| | | |
|---|---|---|
| 0191615 | 8/1986 | European Pat. Off. . |
| 3545615 | 7/1986 | Fed. Rep. of Germany . |
| 62-227932 | 10/1987 | Japan .................................. 428/905 |
| 2169129 | 7/1986 | United Kingdom . |

OTHER PUBLICATIONS

Instructions for Sirocraft Pretty Petals ® No. 3R-30 Silky Sweetheart Rose Kit.
R. K. Iler, *The Chemistry of Silica*, John Wiley & Sons, New York (1979), pp. 15–29, 172–176, 218–233, 364–365, 462–465, 554–564, and 578–579.

*Primary Examiner*—Henry F. Epstein
*Attorney, Agent, or Firm*—George D. Morris

[57] ABSTRACT

An artificial flower comprises at least one petal of microporous material which comprises a matrix consisting essentially of linear ultrahigh molecular weight polyolefin, a large proportion of finely divided water-insoluble siliceous filler, and interconnecting pores, and which microporous material has regions of stretch-induced molecularly oriented polymer in the matrix.

27 Claims, 2 Drawing Sheets

ARTIFICIAL FLOWER

This application is a continuation-in-part of Application Ser. No. 110,147, filed Oct. 19, 1987 now abandoned.

The present invention is directed to an artificial flower comprising one or more artificial petals of microporous material characterized by both a very large proportion of finely divided particulate substantially water-insoluble siliceous filler and a very high void content, and to methods for making the same. Most often the microporous material has a thickness in the range of from about 0.03 to about 0.25 millimeter, and in this form it exhibits high degrees of suppleness and softness to the touch which are surprisingly and wholly unexpected in view of the very large amount of inorganic filler present. Thicknesses somewhat greater than 0.25 millimeter can be used, but the suppleness and softness will normally not be as great as those of the thinner material. The petals may optionally contain perfume and/or colorant when desired. The petals may optionally be printed to add background color, shading, highlights, veins, advertising text, graphics, or the like to any, some, or all of the petals.

BRIEF DESCRIPTION OF THE DRAWINGS

For a better understanding of the invention, reference may be made to the drawings which illustrate various parts of an embodiment of the invention as well as the completed embodiment, and which will be described in detail in conjunction with Example 27. In the drawings, like numerals refer to like parts and.

Figure 1:
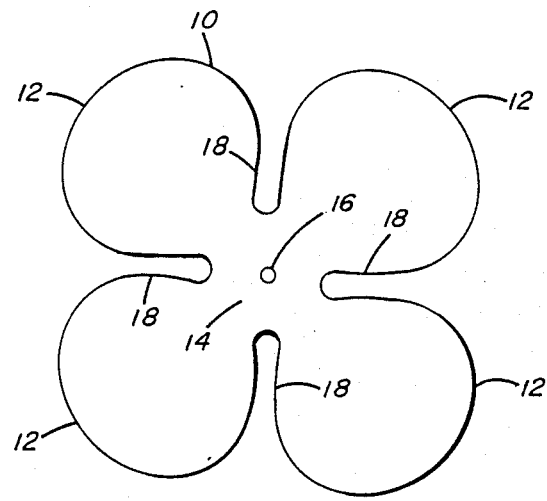
FIG. 1 shows diagrammatically an artificial petal element.

One embodiment of the invention is an artificial flower comprising at least one artificial petal of microporous material wherein the microporous material comprises: (a) a matrix consisting essentially of essentially linear ultrahigh molecular weight polyolefin which is essentially linear ultrahigh molecular weight polyethylene having a intrinsic viscosity of at least about 18 deciliters/gram, essentially linear ultrahigh molecular weight polypropylene having an intrinsic viscosity of at least about 6 deciliters/gram, or a mixture thereof; the matrix comprising regions of stretch-induced molecularly oriented ultrahigh molecular weight polyolefin distributed throughout the matrix, (b) finely divided particulate substantially water-insoluble siliceous filler distributed throughout the matrix, the filler constituting from about 50 percent to about 90 percent by weight of the microporous material, and (c) a network of interconnecting pores communicating throughout the microporous material, the pores constituting more than 80 percent by volume of the microporous material.

In a preferred embodiment, all artificial petals of the artificial flower are of the microporous material.

THE MICROPOROUS MATERIAL

The microporous material from which the artificial petals are made, may be produced by stretching precursor microporous material in at least one stretching direction to a stretch ratio of at least about 1.5, the precursor microporous material comprising (a) a matrix consisting essentially of essentially linear ultrahigh molecular weight polyolefin which is essentially linear ultrahigh molecular weight polyethylene having an intrinsic viscosity of at least about 18 deciliters/gram, essentially linear ultrahigh molecular weight polypropylene having an intrinsic viscosity of at least about 6 deciliters/gram, or a mixture thereof, (b) finely divided particulate substantially water-insoluble siliceous filler distributed throughout the matrix, the filler constituting from about 50 percent to about 90 percent by weight of said microporous material, and (c) a network of interconnecting pores communicating throughout the precursor microporous material, the pores constituting from about 35 percent to about 80 percent by volume of the precursor microporous material, to produce stretched microporous material which is dimensionally stable at room temperature, which has a stretch ratio in the stretching direction of at least about 1.5, and which comprises (d) a matrix consisting essentially of the essentially linear ultrahigh molecular weight polyolefin, the matrix of the stretched microporous material comprising regions of stretch-induced molecularly oriented ultrahigh molecular weight polyolefin distributed throughout the matrix of the stretched microporous material, (e) the filler distributed throughout the matrix of the stretched microporous material, and (f) a network of interconnecting pores communicating throughout the stretched microporous material, the pores of the stretched microporous material constituting more than 80 percent by volume of the stretched microporous material.

It will be appreciated from the above that the stretching both increases the void volume of the material and induces regions of molecular orientation in the ultrahigh molecular weight (UHMW) polyolefin. As is well known in the art, many of the physical properties of molecularly oriented thermoplastic organic polymer, including tensile strength, tensile modulus, Young's modulus, and others, differ considerably from those of the corresponding thermoplastic organic polymer having little or no molecular orientation. Although it is not desired to be bound by any theory, it is believed that the properties of the UHMW polyolefin, the regions of molecular orientation, the high levels of filler loading, and the high degrees of porosity cooperate to provide many of the desirable properties characteristic of the microporous material.

The microporous material is non-isotropic, that is, the pore or microvoid shapes and distributions of pore or microvoid sizes are not the same in planes perpendicular to the surface as in planes parallel to the surface.

Inasmuch as UHMW polyolefin is not a thermoset polymer having an infinite molecular weight, it is technically classified as a thermoplastic. However, because the molecules are essentially very long chains, UHMW polyolefin, and especially UHMW polyethylene, softens when heated but does not flow as a molten liquid in a normal thermoplastic manner. The very long chains and the peculiar properties they provide to UHMW polyolefin are believed to contribute in large measure to the desirable properties of the microporous material.

As indicated earlier, the intrinsic viscosity of the UHMW polyethylene is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 18 to about 39 deciliters/gram. An intrinsic viscosity in the range of from about 18 to about 32 deciliters/gram is preferred.

Also as indicated earlier the intrinsic viscosity of the UHMW polypropylene is at least about 6 deciliters/gram. In many cases the intrinsic viscosity is at least about 7 deciliters/gram. Although there is no particular restriction on the upper limit of the intrinsic viscosity, the intrinsic viscosity is often in the range of from about 6 to about 18 deciliters/gram. An intrinsic viscosity in the range of from about 7 to about 16 deciliters/gram is preferred.

As used herein and in the claims, intrinsic viscosity is determined by extrapolating to zero concentration the reduced viscosities or the inherent viscosities of several dilute solutions of the UHMW polyolefin where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMW polyolefin are ascertained from relative viscosities obtained at 135° C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

The nominal molecular weight of UHMW polyethylene is empirically related to the intrinsic viscosity of the polymer according to the equation:

$$M = 5.37 \times 10^4 [\eta]^{1.37}$$

where M is the nominal molecular weight and $[\eta]$ is the intrinsic viscosity of the UHMW polyethylene expressed in deciliters/gram. Similarly, the nominal molecular weight of UHMW polypropylene is empirically related to the intrinsic viscosity of the polymer according to the equation:

$$M = 8.88 \times 10^4 [\eta]^{1.25}$$

where M is the nominal molecular weight and $[\eta]$ is the intrinsic viscosity of the UHMW polypropylene expressed in deciliters/gram.

The essentially linear ultrahigh molecular weight polypropylene is most frequently essentially linear ultrahigh molecular weight isotactic polypropylene. Often the degree of isotacticity of such polymer is at least about 95 percent, while preferably it is at least about 98 percent.

Sufficient UHMW polyolefin should be present in the matrix to provide its properties to the microporous material. Other thermoplastic organic polymer may also be present in the matrix so long as its presence does not materially affect the properties of the microporous material in an adverse manner. The amount of the other thermoplastic polymer which may be present depends upon the nature of such polymer. In general, a greater amount of other thermoplastic organic polymer may be used if the molecular structure contains little branching, few long sidechains, and few bulky side groups, than when there is a large amount of branching, many long sidechains, or many bulky side groups. For this reason, the preferred thermoplastic organic polymers which may optionally be present are low density polyethylene, high density polyethylene, poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc or the like. It is our experience that usually at least about 70 percent UHMW polyolefin, based on the weight of the matrix, will Provide the desired properties to the microporous material. In most cases, however, it is preferred that the other thermoplastic organic polymer be substantially absent.

The finely divided substantially water-insoluble siliceous filler used in the present invention is particulate. As present in the microporous material, the filler may be in the form of ultimate particles, aggregates of ultimate particles, or a combination of both. In most cases, at least about 90 percent by weight of the filler used in preparing the microporous material has gross particle sizes in the range of from about 5 to about 40 micrometers as determined by use of a Model TAII Coulter Counter (Coulter Electronics, Inc.) according to ASTM C 690-80 but modified by stirring the filler for 10 minutes in Isoton II electrolyte (Curtin Matheson Scientific, Inc.) using a four-blade, 4.445 centimeter diameter propeller stirrer. Preferably at least about 90 percent by weight of the filler has gross particle sizes in the range of from about 10 to about 30 micrometers. It is expected that the sizes of filler agglomerates will be reduced during processing of the ingredients to prepare the microporous material. Accordingly, the distribution of gross particle sizes in the microporous material may be smaller than in the raw filler itself. ASTM C 690-80 is, in its entirety, incorporated herein by reference.

Examples of suitable siliceous fillers include silica, mica, montmorillonite, kaolinite, asbestos, talc, diatomaceous earth, vermiculite, natural and synthetic zeolites, cement, calcium silicate, aluminum silicate, sodium aluminum silicate, aluminum polysilicate, alumina silica gels, and glass particles. In addition to the siliceous fillers other finely divided particulate substantially water-insoluble fillers may also be employed. Examples of such optional fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate.

Silica and the clays are the preferred siliceous fillers. Of the silicas, precipitated silica, silica gel, or fumed silica is most often used.

The particularly preferred finely divided particulate substantially water-insoluble siliceous filler is precipitated silica. Although both are silicas, it is important to distinguish precipitated silica from silica gel inasmuch as these different materials have different properties. Reference in this regard is made to R. K. Iler, *The Chemistry of Silica*, John Wiley & Sons, New York (1979), Library of Congress Catalog No. QD 181.S6144, the entire disclosure of which is incorporated herein by reference. Note especially pages 15–29, 172–176, 218–233, 364–465, 462–465, 554–564, and 578–579. Silica gel is usually produced commercially at low pH by acidifying an aqueous solution of a soluble metal silicate, typically sodium silicate, with acid. The acid employed is generally a strong mineral acid such as sulfuric acid or hydrochloric acid although carbon dioxide is sometimes used. Inasmuch as there is essentially no difference in density between gel phase and the surrounding liquid phase while the viscosity is low, the gel phase does not settle out, that is to say, it does not precipitate. Silica gel, then, may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight, although the highly hydrated forms are only rarely used in the present invention.

Precipitated silica is usually produced commercially by combining an aqueous solution of a soluble metal silicate, ordinarily alkali metal silicate such as sodium silicate, and an acid so that colloidal particles will grow in weakly alkaline solution and be coagulated by the alkali metal ions of the resulting soluble alkali metal salt. Various acids may be used, including the mineral acids, but the preferred acid is carbon dioxide. In the absence of a coagulant, silica is not precipitated from solution at any pH. The coagulant used to effect precipitation may be the soluble alkali metal salt produced during formation of the colloidal silica particles, it may be added electrolyte such as a soluble inorganic or organic salt, or it may be a combination of both.

Precipitated silica, then, may be described as precipitated aggregates of ultimate particles of colloidal amorphous silica that have not at any point existed as macroscopic gel during the preparation. The sizes of the aggregates and the degree of hydration may vary widely.

Precipitated silica powders differ from silica gels that have been pulverized in ordinarily having a more open structure, that is, a higher specific pore volume. However, the specific surface area of precipitated silica as measured by the Brunauer, Emmett, Teller (BET) method using nitrogen as the adsorbate, is often lower than that of silica gel.

Many different precipitated silicas may be employed in the present invention, but the preferred precipitated silicas are those obtained by precipitation from an aqueous solution of sodium silicate using a suitable acid such as sulfuric acid, hydrochloric acid, or carbon dioxide. Such precipitated silicas are themselves known and processes for producing them are described in detail in U.S. Pat. No. 2,940,830 and in West German Offenlegungsschrift No. 35 45 615, the entire disclosures of which are incorporated herein by reference, including especially the processes for making precipitated silicas and the properties of the products.

In the case of the preferred filler, precipitated silica, the average ultimate particle size (irrespective of whether or not the ultimate particles are agglomerated) is less than about 0.1 micrometer as determined by transmission electron microscopy. Often the average ultimate particle size is less than about 0.05 micrometer. Preferably the average ultimate particle size of the precipitated silica is less than about 0.03 micrometer.

The finely divided particulate substantially water-insoluble siliceous filler constitutes from about 50 to about 90 percent by weight of the microporous material. Frequently such filler constitutes from about 50 percent to about 85 percent by weight of the microporous material. From about 60 percent to about 80 percent by weight is preferred.

Minor amounts, usually less than about 5 percent by weight, of other materials used in processing such as lubricant, plasticizer, processing plasticizer, organic extraction liquid, surfactant, water, and the like, may optionally also be present. Yet other materials introduced for particular purposes may optionally be present in the microporous material in small amounts, usually less than about 15 percent by weight. Examples of such materials include antioxidants, ultraviolet light absorbers, flame retardants, dyes, pigments, and the like. The balance of the microporous material, exclusive of filler and any impregnant applied for one or more special purposes, is essentially the thermoplastic organic polymer.

On an impregnant-free basis, pores constitute more than 80 percent by volume of the microporous material. In many instances the pores constitute at least about 85 percent by volume of the microporous material. Often the pores constitute from more than 80 percent to about 95 percent by volume of the microporous material. From about 85 percent to about 95 percent by volume is preferred. As used herein and in the claims, the porosity (also known as void volume) of the microporous material, expressed as percent by volume, is determined according to the equation:

$$Porosity = 100[1 - d_1/d_2]$$

where $d_1$ is the density of the sample which is determined from the sample weight and the sample volume as ascertained from measurements of the sample dimensions and $d_2$ is the density of the solid portion of the sample which is determined from the sample weight and the volume of the solid portion of the sample. The volume of the solid portion of the sample is determined using a Quantachrome Stereopycnometer (Quantachrome Corp.) in accordance with the accompanying operating manual.

The volume average diameter of the pores of the microporous sheet is determined by mercury porosimetry using an Autoscan mercury porosimeter (Quantachrome Corp.) in accordance with the accompanying operating manual. The volume average pore radius for a single scan is automatically determined by the porosimeter. In operating the porosimeter, a scan is made in the high pressure range (from about 138 kilopascals absolute to about 227 megapascals absolute). If about 2 percent or less of the total intruded volume occurs at the low end (from about 138 to about 250 kilopascals absolute) of the high pressure range, the volume average pore diameter is taken as twice the volume average pore radius determined by the porosimeter. Otherwise, an additional scan is made in the low pressure range (from about 7 to about 165 kilopascals absolute) and the volume average pore diameter is calculated according to the equation:

$$d = 2\left(\frac{v_1 r_1}{w_1} + \frac{v_2 r_2}{w_2}\right) / \left(\frac{v_1}{w_1} + \frac{v_2}{w_2}\right)$$

where $d$ is the volume average pore diameter, $v_1$ is the total volume of mercury intruded in the high pressure range, $v_2$ is the total volume of mercury intruded in the low pressure range, $r_1$ is the volume average pore radius determined from the high pressure scan, $r_2$ is the volume average pore radius determined from the low pressure scan, $w_1$ is the weight of the sample subjected to the high pressure scan, and $w_2$ is the weight of the sample subjected to the low pressure scan. Generally the volume average diameter of the pores is in the range of from about 0.6 to about 50 micrometers. Very often the volume average diameter of the Pores is in the range of from about 1 to about 40 micrometers. From about 2 to about 30 micrometers is preferred.

In the course of determining the volume average pore diameter by the above procedure, the maximum pore radius detected is sometimes noted. This is taken from the low pressure range scan if run; otherwise it is taken from the high pressure range scan. The maximum pore diameter is twice the maximum pore radius.

The microporous sheet may be produced by stretching precursor microporous material according to the method described briefly above and in more detail below.

The precursor microporous material may be produced according to the general principles and procedures of U.S. Pat. No. 3,351,495, the entire disclosure of which is incorporated herein by reference, including especially the processes for making microporous materials and the properties of the products.

Preferably filler, thermoplastic organic polymer powder, processing plasticizer and minor amounts of lubricant and antioxidant are mixed until a substantially uniform mixture is obtained. The weight ratio of filler to polymer powder employed in forming the mixture is essentially the same as that of the precursor microporous material and that of the stretched microporous material to be produced. The mixture, together with additional processing plasticizer, is introduced to the heated barrel of a screw extruder. Attached to the extruder is a sheeting die. A continuous sheet formed by the die is forwarded without drawing to a pair of heated calender rolls acting cooperatively to form continuous sheet of lesser thickness than the continuous sheet exiting from the die. The continuous sheet from the calender then passes to a first extraction zone where the processing plasticizer is substantially removed by extraction with an organic liquid which is a good solvent for the processing plasticizer, a poor solvent for the organic polymer, and more volatile than the processing plasticizer. Usually, but not necessarily, both the processing plasticizer and the organic extraction liquid are substantially immiscible with water. The continuous sheet then passes to a second extraction zone where the residual organic extraction liquid is substantially removed by steam and/or water. The continuous sheet is then passed through a forced air dryer for substantial removal of residual water and remaining residual organic extraction liquid. From the dryer the continuous sheet, which is precursor microporous material, is passed to a take-up roll.

The processing plasticizer has little solvating effect on the thermoplastic organic polymer at 60° C., only a moderate solvating effect at elevated temperatures on the order of about 100° C., and a significant solvating effect at elevated temperatures on the order of about 200° C. It is a liquid at room temperature and usually it is processing oil such as paraffinic oil, naphthenic oil, or an aromatic oil. Suitable processing oils include those meeting the requirements of ASTM D 2226-82, Types 103 and 104. Preferred are those oils which have a pour point of less than 22° C. according to ASTM D 97-66 (reapproved 1978). Particularly Preferred are oils having a pour point of less than 10° C. Examples of suitable oils include Shellflex® 412 and Shellflex® 371 oil (Shell Oil Co.) which are solvent refined and hydrotreated oils derived from naphthenic crude. ASTM D 2226-82 and ASTM D 97-66 (reapproved 1978) are, in the entireties, incorporated herein by reference. It is expected that other materials, including the phthalate ester plasticizers such as dibutyl phthalate, bis(2-ethylhexyl) phthalate, diisodecyl phthalate, dicyclohexyl phthalate, butyl benzyl phthalate, and ditridecyl phthalate, will function satisfactorily as processing plasticizers.

There are many organic extraction liquids that can be used. Examples of suitable organic extraction liquids include 1,1,2-trichloroethylene, perchloroethylene, 1,2-dichloroethane, 1,1,1-trichloroethane, 1,1,2-trichloroethane, methylene chloride, chloroform, isopropyl alcohol, diethyl ether, and acetone.

In the above described process for producing precursor microporous material, extrusion and calendering are facilitated when the substantially water-insoluble filler carries much of the processing plasticizer. The capacity of the filler particles to absorb and hold the processing plasticizer is a function of the surface area of the filler. It is therefore preferred that the filler have a high surface area. High surface area fillers are materials of very small particle size, materials having a high degree of porosity or materials exhibiting both characteristics. Usually the surface area of the filler itself is in the range of from about 20 to about 400 square meters per gram as determined by the Brunauer, Emmett, Teller (BET) method according to ASTM C 819-77 using nitrogen as the adsorbate but modified by outgassing the system and the sample for one hour at 130° C. Preferably the surface area is in the range of from about 25 to about 350 square meters per gram. ASTM C 819-77 is, in its entirety, incorporated herein by reference.

Inasmuch as it is desirable to essentially retain the filler in the precursor microporous sheet, it is preferred that the substantially water-insoluble filler be substantially insoluble in the processing Plasticizer and substantially insoluble in the organic extraction liquid when precursor microporous material is produced by the above process.

The precursor microporous material comprises finely divided substantially water-insoluble siliceous filler, thermoplastic organic polymer which consists essentially of the UHMW polyolefin, and optional materials in essentially the same weight proportions as those discussed above in respect of the stretched sheet. The residual processing plasticizer content is usually less than 5 percent by weight of the precursor microporous sheet and this may be reduced even further by additional extractions using the same or a different organic extraction liquid.

Pores constitute from about 35 to about 80 percent by volume of the precursor microporous material. In many cases the pores constitute from about 60 to about 75 percent by volume of the precursor microporous material. The porosity of the precursor microporous material, expressed as percent by volume, is determined by the same procedure described above in respect of the stretched microporous material. In all cases, the porosity of the microporous material is, unless impregnated after stretching, greater than that of the precursor microporous material.

The volume average diameter of the pores of the precursor microporous material as determined by the mercury porosimetry method previously described in respect of the stretched microporous material, is usually in the range of from about 0.02 to about 0.5 micrometers. Frequently the average diameter of the pores is in the range of from about 0.04 to about 0.3 micrometers. From about 0.05 to about 0.25 micrometers is preferred.

The microporous material may be produced by stretching the precursor microporous material in at least one stretching direction to a stretch ratio of at least about 1.5. In many cases the stretch ratio is at least about 1.7. Preferably it is at least about 2. Frequently the stretch ratio is in the range of from about 1.5 to about 15. Often the stretch ratio is in the range of from about 1.7 to about 10. Preferably the stretch ratio is in the range of from about 2 to about 6. As used herein and in the claims, the stretch ratio is determined by the formula:

$$S = L_2/L_1$$

where S is the stretch ratio, $L_1$ is the distance between two reference points located on the precursor microporous material and on a line parallel to the stretching direction, and $L_2$ is the distance between the same two reference points located on the stretched microporous material.

The temperatures at which stretching is accomplished may vary widely. Stretching may be accomplished at about ambient room temperature, but usually elevated temperatures are employed. The precursor microporous material may be heated by any of a wide variety of techniques prior to, during, and/or after stretching. Examples of these techniques include radiative heating such as that provided by electrically heated or gas fired infrared heaters, convective heating such as that provided by recirculating hot air, and conductive heating such as that provided by contact with heated rolls. The temperatures which are measured for temperature control purposes may vary according to the apparatus used and personal preference. For example, temperature-measuring devices may be placed to ascertain the temperatures of the surfaces of infrared heaters, the interiors of infrared heaters, the air temperatures of points between the infrared heaters and the precursor microporous material, the temperatures of circulating hot air at points within the apparatus, the temperature of hot air entering or leaving the apparatus, the temperatures of the surfaces of rolls used in the stretching process, the temperature of heat transfer fluid entering or leaving such rolls, or film surface temperatures, In general, the temperature or temperatures are controlled such that the precursor microporous material is stretched about evenly so that the variations, if any, in film thickness of the stretched microporous material are within acceptable limits and so that the amount of stretched microporous material outside of those limits is acceptably low. It will be apparent that the temperatures used for control purposes may or may not be close to those of the precursor microporous material itself since they depend upon the nature of the apparatus used, the locations of the temperature-measuring devices, and the identities of the substances or objects whose temperatures are being measured.

In view of the locations of the heating devices and the line speeds usually employed during stretching, gradients of varying temperatures may or may not be present through the thickness of the precursor microporous material. Also because of such line speeds, it is impracticable to measure these temperature gradients. The presence of gradients of varying temperatures, when they occur, makes it unreasonable to refer to a single film temperature. Accordingly, film surface temperatures, which can be measured, are best used for characterizing the thermal condition of the precursor microporous material. These are ordinarily about the same across the width of the precursor microporous material during stretching although they may be intentionally varied, as for example, to compensate for precursor microporous material having a wedge-shaped cross-section across the sheet. Film surface temperatures along the length of the sheet may be about the same or they may be different during stretching.

The film surface temperatures at which stretching is accomplished may vary widely, but in general they are such that the precursor microporous material is stretched about evenly, as explained above. In most cases, the film surface temperatures during stretching are in the range of from about 20° C. to about 220° C. Often such temperatures are in the range of from about 50° C. to about 200° C. From about 75° C. to about 180° C. is preferred.

Stretching may be accomplished in a single step or a plurality of steps as desired. For example, when the precursor microporous material is to be stretched in a single direction (uniaxial stretching), the stretching may be accomplished by a single stretching step or a sequence of stretching steps until the desired final stretch ratio is attained. Similarly, when the precursor microporous material is to be stretched in two directions (biaxial stretching), the stretching can be conducted by a single biaxial stretching step or a sequence of biaxial stretching steps until the desired final stretch ratios are attained. Biaxial stretching may also be accomplished by a sequence of one or more uniaxial stretching steps in one direction and one or more uniaxial stretching steps in another direction. Biaxial stretching steps where the precursor microporous material is stretched simultaneously in two directions and uniaxial stretching steps may be conducted in sequence in any order. Stretching in more than two directions is within contemplation. It may be seen that the various permutations of steps are quite numerous. Other steps, such as cooling, heating, sintering, annealing, reeling, unreeling, and the like, may optionally be included in the overall process as desired.

Various types of stretching apparatus are well known and may be used to accomplish stretching of the precursor microporous material according to the present invention. Uniaxial stretching is usually accomplished by stretching between two rollers wherein the second or downstream roller rotates at a greater peripheral speed than the first or upstream roller. Uniaxial stretching can also be accomplished on a standard tentering machine. Biaxial stretching may be accomplished by simultaneously stretching in two different directions on a tentering machine. More commonly, however, biaxial stretching is accomplished by first uniaxially stretching between two differentially rotating rollers as described above, followed by either uniaxially stretching in a different direction using a tenter machine or by biaxially stretching using a tenter machine. The most common type of biaxial stretching is where the two stretching directions are approximately at right angles to each other. In most cases where continuous sheet is being stretched, one stretching direction is at least approximately parallel to the long axis of the sheet (machine direction) and the other stretching direction is at least approximately perpendicular to the machine direction and is in the plane of the sheet (transverse direction).

After stretching has been accomplished, the microporous material may optionally be sintered, annealed, heat set and/or otherwise heat treated. During these optional steps, the stretched microporous material is usually held under tension so that it will not markedly shrink at the elevated temperatures employed, although some relaxation amounting to a small fraction of the maximum stretch ratio is frequently permitted.

Following stretching and any heat treatments employed, tension is released from the stretched microporous material after the microporous material has been brought to a temperature at which, except for a small amount of elastic recovery amounting to a small fraction of the stretch ratio, it is essentially dimensionally stable in the absence of tension. Elastic recovery under these conditions usually does not amount to more than about 10 percent of the stretch ratio.

The stretched microporous material may then be further processed as desired. Examples of such further processing steps include reeling, cutting, stacking, treatment to remove residual processing plasticizer or extraction solvent, impregnation with various materials, and fabrication into shapes for various end uses.

The precursor microporous materials, the microporous materials, and methods for their production are further described in conjunction with the following examples which are to be considered illustrative rather than limiting.

EXAMPLES

Precursor Sheet Formation

The preparation of the above described materials is illustrated by the following descriptive examples. Processing oil was used as the processing plasticizer. Silica, polymer, lubricant and antioxidant in the amounts specified in Table I were placed in a high intensity mixer and mixed at high speed for 30 seconds to thoroughly blend the dry ingredients. The processing oil needed to formulate the batch was pumped into the mixer over a period of 2–3 minutes with low speed agitation. After the completion of the processing oil addition a 2 minute low speed mix period was used to distribute the processing oil uniformly throughout the mixture.

TABLE I

| Example | Formulations | | |
|---|---|---|---|
| | 1 | 2 | 3 |
| Ingredient | | | |
| UHMWPE (1), kg | 5.67 | 9.98 | 4.25 |
| Polypropylene (2), kg | 0 | 0 | 1.42 |
| Silica (3), kg | 19.96 | 19.96 | 19.96 |
| Lubricant (4), g | 100 | 100 | 100 |
| Antioxidant (5), g | 100 | 100 | 100 |
| Processing Oil (6), kg | | | |
| in Batch | 31.21 | 31.21 | 31.21 |
| at Extruder | 13.61 | 41.59 | 30.39 |

(1) UHMWPE = Ultrahigh Molecular Weight Polyethylene, Himont 1900, Himont, U.S.A., Inc.
(2) Profax ® 6801, Himont U.S.A., Inc.
(3) HiSil ® SBG, PPG Industries, Inc.
(4) Petrac ® CZ81, Desoto, Inc., Chemical Speciality Division
(5) Irganox ® B-215, Ciba-Geigy Corp.
(6) Shellflex ® 412, Shell Chemical Co.

The batch was then conveyed to a ribbon blender where it was mixed with up to two additional batches of the same composition. Material was fed from the ribbon blender to a twin screw extruder by a variable rate screw feeder. Additional processing oil was added via a metering pump into the feed throat of the extruder. The extruder mixed and melted the formulation and extruded it through a 76.2 centimeter ×0.3175 centimeter slot die. The extruded sheet was then calendered. A description of one type of calender that may be used may be found in the U.S. Pat. No. 4,734,229, the entire disclosure of which is incorporated herein by reference, including the structures of the devices and their modes of operation. Other calenders of different design may alternatively be used; such calenders and their modes of operation are well known in the art. The hot, calendered sheet was then passed around a chill roll to cool the sheet. The rough edges of the cooled calendered sheet were trimmed by rotary knives to the desired width.

The oil filled sheet was conveyed to the extractor unit where it was contacted by both liquid and vaporized 1,1,2-trichloroethylene (TCE). The sheet was transported over a series of rollers in a serpentine fashion to provide multiple, sequential vapor/liquid/vapor contacts. The extraction liquid in the sump was maintained at a temperature of 65–88° C. Overflow from the sump of the TCE extractor was returned to a still which recovered the TCE and the processing oil for reuse in the process. The bulk of the TCE was extracted from the sheet by steam as the sheet was passed through a second extractor unit. A description of these types of extractors may be found in European Pat. Application Publication No. EP 0 191 615, the entire disclosure of which is incorporated herein by reference, including especially the structures of the devices and their modes of operation. The sheet was dried by radiant heat and convective air flow. The dried sheet was wound on cores to provide roll stock for further processing.

The three precursor microporous sheets, as well as the hereinafter described biaxially stretched microporous sheets produced therefrom, were tested for various physical properties. Table II identifies the properties with the methods used for their determination. The various ASTM and TAPPI test methods and Method 502 C, referenced in Table II, are, in their entireties, incorporated herein by reference. The results of physical testing of the three precursor microporous sheets are shown in Table III.

Property values indicated by MD (machine direction) were obtained on samples whose major axis was oriented along the length of the sheet. TD (transverse direction; cross machine direction) properties were obtained from samples whose major axis was oriented across the sheet.

TABLE II

Physical Test Methods

| Property | Test Method |
|---|---|
| Tensile Strength | ASTM D 412-83. |
| Elongation | |
| Porosity | As described in the text above. |
| Matrix Tensile Strength | Tensile Strength determined in accordance with ASTM D 412-83 multiplied by the quantity 100/(100-Porosity). |
| Tear Strength, Die C | ASTM D 624-81. |
| Processing Oil Content | Method 502 C in "Standard Methods for the Examination of Water and Wastewater", 14th Ed., APHA-AWWA-WPCF (1975). |
| Maximum Pore Diameter | Mercury Porosimetry, as described in the text above. |
| Volume Average Pore Diameter | Mercury Porosimetry, as described in the text above. |
| Gurley Air Flow | ASTM D 726-58 (reapproved 1971), Method A. |
| Opacity | TAPPI Standard T 425 (Contrast Ratio) using Illuminant C instead of Illuminant A. |
| Brightness | TAPPI Standard T 452. |
| Mullens Hydrostatic Resistance | ASTM D 751-79, Sec. 30-34, Method A. |
| MVTR (Moisture Vapor Transmission Rate) | ASTM E 96-80. |
| Methanol Bubble Pressure | ASTM F 316-80, using methanol. |
| Maximum Limiting Pore Diameter | ASTM F-316-80, using methanol where $cY = 22.34$ ($\mu$m)(kPa). |
| Heat Shrinkage | ASTM D 1204-84, using 15.24 cm × 20.32 cm sample, 1 hr at 100° C. |
| Strip Tensile Strength and Elongation | ASTM D 828-60. |
| Breaking Factor and Elongation | ASTM D 882-83. |

TABLE III

Physical Properties of Precursor Microporous Sheet

| Example | 1 | 2 | 3 |
|---|---|---|---|
| Thickness, mm | 0.229 | 0.279 | 0.229 |
| Matrix Tensile Strength, MPa | | | |
| MD | 23.82 | 34.33 | 25.66 |
| TD | 9.94 | 14.91 | 10.38 |
| Elongation at Break, % | | | |
| MD | 250 | 279 | 227 |
| TD | 108 | 140 | 112 |
| Tear Strength, kN/m | | | |
| MD | 36.25 | 61.47 | 47.81 |
| TD | 18.04 | 39.93 | 23.12 |
| Porosity, vol % | 71 | 66 | 68 |
| Processing Oil Content, wt % | 4.1 | 2.7 | 2.4 |
| Maximum Pore Diameter, $\mu$m | 0.86 | 0.30 | 0.28 |
| Volume Average Pore Diameter, $\mu$m | 0.11 | 0.065 | 0.069 |
| Gurley Air Flow, sec/100 cc | 904 | 1711 | 955 |
| Opacity, % | 96.0 | 95.1 | 94.4 |
| Brightness, % | 87.8 | 92.6 | 92.0 |

Biaxial Stretching of Precursor Microporous Sheet

The precursor materials produced in Examples 1-3 were unwound from cores and biaxially stretched by first uniaxially stretching in the machine direction using a single stage roll-to-roll machine direction stretching (MDS) unit and then essentially uniaxially stretching in the transverse direction using a moving clip tenter frame as a transverse direction stretching (TDS) unit. A preheat roll was employed with the MDS unit to heat the sheet prior to stretching. In the TDS unit, the sheet was heated by banks of infrared radiant heaters. The Preheat and Stretch I Zones of the TDS Unit each contained both upper and lower banks of such heaters. The upper banks were located about 10.16 centimeters above the precursor microporous material while the lower banks were located about 15.24 centimeters below the precursor microporous material. Electrical power to the heaters of each lower bank was controlled by an on-off controller in response to the difference between a set point and the signal provided by a thermocouple mounted in one heater of the bank. Autotransformers were used to adjust electrical power to the heaters of the upper banks. The Stretch II, Stretch III, Sinter I, and Sinter II Zones each contained upper banks of infrared radiant heaters located about 10.16 centimeters above the precursor microporous material. There were no lower banks in these zones. Electrical power to the heaters of each upper bank was controlled as described in respect of the heaters of each lower bank in the preheat and Stretch I Zones. For a description of a typical TDS unit, see FIG. 2 and column 2, lines 43-69, of U.S. Pat. No. 2,823,421, the entire disclosure of which is incorporated herein by reference.

The MDS stretch ratio was varied by controlling the relative peripheral speeds of the feed rolls and the take-off rolls of the MDS unit. The chain track positions in the tenter frame were set to achieve the desired stretch ratio and then to essentially maintain that stretch ratio during sintering. For each of Examples 4-25, the settings of one of the last four vertical columns in Table IV were employed. The correct column may be ascertained by matching up the TD stretch ratio of the example with the final stretch ratio of the column.

TABLE IV

| | Transverse Direction Stretching | | | | |
|---|---|---|---|---|---|
| Zone | Cumulative Distance from Beginning of Oven, meters | Transverse Stretch Ratio | | | |
| | 0 | 1 | 1 | 1 | 1 |
| Preheat | 2.794 | 1 | 1 | 1 | 1 |
| Stretch I | 4.318 | 1.33 | 1.44 | 1.65 | 1.87 |
| Stretch II | 8.890 | 2.31 | 2.75 | 3.62 | 4.49 |

TABLE IV-continued

Transverse Direction Stretching

| Zone | Cumulative Distance from Beginning of Oven, meters | Transverse Stretch Ratio | | | |
|---|---|---|---|---|---|
| Stretch III | 9.779 | 2.5 | 3 | 4 | 5 |
| Sinter I | 11.430 | 2.5 | 3 | 4 | 5 |
| Sinter II | 13.716 | 2.5 | 3 | 4 | 5 | machine direction speed of the TDS unit. The linear feed rate from the roll stock of precursor microporous material to the MDS unit was set at a value given by the line speed divided by the MDS stretch ratio. Thus, with a line speed of 24 m/min and a MDS stretch ratio of 2, the linear feed rate from the roll stock to the MDS unit would be 12 m/min. The properties of several representative examples of biaxially stretched sheets are given in Tables V-VII.

TABLE V

Properties of Biaxially Stretched Microporous Sheets Produced from Precursor Sheet of Example 1

| Example No. | 4 | 5 | 6 | 7 | 8 | 9 | 10 | 11 | 12 |
|---|---|---|---|---|---|---|---|---|---|
| Thickness, mm | 0.178 | 0.152 | 0.127 | 0.076 | 0.076 | 0.102 | 0.127 | 0.102 | 0.076 |
| Stretch Ratio | | | | | | | | | |
| MD | 2 | 2 | 2 | 2 | 3 | 3 | 3 | 3 | 3 |
| TD | 3 | 3 | 4 | 5 | 3 | 3 | 3 | 3 | 4 |
| Line Speed m/min | 48.8 | 24.4 | 24.4 | 24.4 | 24.4 | 24.4 | 24.4 | 24.4 | 24.4 |
| MDS Preheat Temp, °C. | 79 | 79 | 79 | 79 | 79 | 79 | 79 | 79 | 79 |
| TDS Average Zonal Set Point Temps., °C. | | | | | | | | | |
| Preheat (lower banks) | 149 | 177 | 177 | 149 | 149 | 149 | 177 | 149 | 177 |
| Stretch I (lower banks) | 149 | 177 | 177 | 149 | 149 | 149 | 177 | 149 | 177 |
| Stretch II | 189 | 171 | 171 | 189 | 189 | 189 | 171 | 189 | 171 |
| Stretch III | 149 | 142 | 142 | 149 | 149 | 149 | 142 | 149 | 142 |
| Sinter I | 149 | 144 | 144 | 149 | 149 | 149 | 144 | 149 | 144 |
| Sinter II | 204 | 227 | 227 | 204 | 149 | 204 | 227 | 260 | 227 |
| Weight, g/m$^2$ | 27 | 24 | 17 | 14 | 14 | 10 | 14 | 14 | 10 |
| Porosity, vol % | 91 | 90 | 92 | 90 | 89 | 93 | 93 | 93 | 91 |
| Matrix Tensile Strength, MPa | | | | | | | | | |
| MD | 53.70 | 32.96 | 40.25 | 25.30 | 29.52 | 62.74 | 67.77 | 41.96 | 56.69 |
| TD | 40.14 | 29.30 | 65.76 | 46.54 | 61.99 | 45.41 | 43.93 | 57.62 | 55.77 |
| Elongation at break, % | | | | | | | | | |
| MD | 57 | 56 | 60 | 67 | 26 | 23 | 34 | 18 | 33 |
| TD | 27 | 41 | 13 | 9 | 23 | 27 | 30 | 31 | 12 |
| Tear Strength, kN/m | | | | | | | | | |
| MD | 9.28 | 5.78 | 7.01 | 3.85 | 2.28 | 5.08 | 6.30 | 5.60 | 5.08 |
| TD | 4.90 | 4.90 | 7.01 | 8.23 | 7.53 | 1.93 | 4.38 | 4.55 | 4.73 |
| Gurley Air Flow, sec/100 cc | 47 | 45 | 40 | 29 | 32 | 28 | 37 | 28 | 36 |
| Mullens Hydrostatic kPa | 483 | 434 | 490 | 448 | 476 | 503 | 496 | 434 | 510 |
| MVTR, g/m$^2$day | 935 | | | | | | | 963 | |
| Methanol Bubble Point Pressure, kPa | 290 | 276 | 296 | 234 | 145 | 276 | 324 | 55 | 317 |
| Maximum Limiting Pore Diameter, μm | 0.077 | 0.081 | 0.075 | 0.095 | 0.154 | 0.081 | 0.069 | 0.404 | 0.070 |
| Maximum Pore Diameter, μm | | | | | | | 155 | | |
| Volume Average Pore Diameter μm | | | | | | | 17.92 | | |
| Heat Shrinkage after 1 hr. at 100° C., % | | | | | | | | | |
| MD | 19.0 | | 9.4 | 12.0 | | 19.3 | 24.1 | 21.2 | |
| TD | 23.2 | | 22.5 | 28.3 | | 25.7 | 29.1 | 30.8 | |

The precursor sheet stock of Examples 1-3 was fed over the preheat roll of the MDS unit which was heated to the temperature indicated in Tables V-VII. The sheet was then stretched to the indicated stretch ratio by maintaining the relative peripheral speeds of the second and first stretch rolls at essentially the same ratio as the stretch ratio. The line speed given in Tables V-VII is the output speed of the MDS unit and the The biaxially stretched microporous sheet of Example 10 was examined by scanning electron microscopy at a magnification of 430X. A section taken in a plane perpendicular to the sheet surface (viz., looking into the thickness) and along the machine direction showed substantial pore elongation. A section taken in a plane perpendicular to the sheet surface and along the transverse direction showed pore elongation which was not as pronounced as along the machine direction. A view of the sheet surface (not sectioned) showed that large void structures were not as numerous as in views of either of the sections looking into the thickness.

void structures were not as numerous as in views of either of the sections looking into the thickness.

TABLE VI

Properties of Biaxially Stretched Microporous Materials Produced from Precursor Sheet of Example 2

| Example No. | 13 | 14 | 15 | 16 | 17 | 18 | 19 | 20 | 21 |
|---|---|---|---|---|---|---|---|---|---|
| Thickness, mm | 0.203 | 0.152 | 0.178 | 0.127 | 0.152 | 0.127 | 0.102 | 0.076 | 0.178 |
| Stretch Ratio | | | | | | | | | |
| MD | 2 | 2 | 2 | 2 | 2 | 3 | 3 | 3 | 3 |
| TD | 2.5 | 3 | 3 | 3 | 4 | 3 | 3 | 3 | 4 |
| Line Speed m/min | 24.4 | 24.4 | 15.2 | 24.4 | 15.2 | 24.4 | 15.2 | 24.4 | 15.2 |
| MDS Preheat Temp., °C. | 104 | 104 | 121 | 79 | 121 | 104 | 121 | 79 | 121 |
| TDS Average Zonal Set Point Temps., °C. | | | | | | | | | |
| Preheat (lower banks) | 177 | 177 | 149 | 149 | 149 | 177 | 149 | 149 | 149 |
| Stretch I (lower banks) | 177 | 177 | 149 | 149 | 149 | 177 | 149 | 149 | 149 |
| Stretch II | 171 | 171 | 188 | 188 | 188 | 171 | 188 | 188 | 188 |
| Stretch III | 142 | 142 | 144 | 149 | 144 | 142 | 144 | 149 | 144 |
| Sinter I | 144 | 144 | 200 | 149 | 144 | 144 | 144 | 149 | 144 |
| Sinter II | 227 | 227 | 255 | 316 | 255 | 227 | 255 | 316 | 255 |
| Weight, g/m$^2$ | 44 | 24 | | | 24 | 17 | | 14 | 31 |
| Porosity, vol % | 86 | 90 | | | 90 | 92 | | 90 | 90 |
| Matrix Tensile Strength, MPa | | | | | | | | | |
| MD | 52.94 | 61.50 | | | 36.61 | 96.18 | | 73.91 | 37.51 |
| TD | 44.47 | 67.98 | | | 109.49 | 54.38 | | 75.01 | 117.21 |
| Elongation at Break, % | | | | | | | | | |
| MD | 58 | 54 | 161 | 41 | 87 | 31 | 13 | 19 | 111 |
| TD | 51 | 39 | 15 | 16 | 9 | 42 | 16 | 16 | 7 |
| Tear Strength, kN/m | | | | | | | | | |
| MD | 20.31 | 12.61 | 17.51 | 6.13 | 13.13 | 12.26 | 8.41 | 5.95 | 18.56 |
| TD | 13.31 | 12.78 | 21.02 | 7.18 | 11.03 | 9.11 | 5.25 | 7.53 | 19.44 |
| Gurley Flow sec/100 cc | 81 | 40 | | | 46 | 45 | | | 52 |
| Mullens Hydrostatic, kPa | 745 | 689 | 676 | 496 | 745 | 717 | 641 | 503 | 703 |
| MVTR, g/m$^2$ day | | | 868 | 761 | | 947 | 913 | 827 | |
| Methanol Bubble Point Pressure, kPa | 290 | 303 | | | 303 | 365 | | | 290 |
| Maximum Limiting Pore Diameter, μm | 0.077 | 0.074 | | | 0.074 | 0.061 | | | 0.077 |
| Maximum Pore Daimeter, μm | | 111 | | | | >146 | | | |
| Volume Average Pore Diameter, μm | | 7.13 | | | | 4.70 | | | |
| Heat Shrinkage after 1 hr. at 100° C., % | | | | | | | | | |
| MD | 11.7 | | 3.8 | 7.1 | 12.3 | | 15.3 | 6.3 | 7.7 |
| TD | 24.4 | | 23.6 | 11.8 | 22.0 | | 34.1 | 18.9 | 21.5 |

The biaxially stretched microporous sheet of Example 18 was examined by scanning electron microscopy at a magnification of 430X. A section taken in a plane perpendicular to the sheet surface (viz., looking into the thickness) and along the machine direction showed substantial pore elongation. A section taken in a plane perpendicular to the sheet surface and along the transverse direction showed pore elongation which was not as pronounced as along the machine direction. A view of the sheet surface (not sectioned) showed that large

TABLE VII

Properties of Biaxially Stretched Microporous Sheets Produced from Precursor Sheet of Example 3

| Example No. | 22 | 23 | 24 | 25 |
|---|---|---|---|---|
| Thickness, mm | 1.178 | 0.102 | 0.127 | 0.102 |
| Stretch Ratio | | | | |
| MD | 2 | 2 | 3 | 3 |
| TD | 3 | 3 | 3 | 4 |
| Line Speed, m/min | 24.4 | 24.4 | 24.4 | 24.4 |
| MDS Preheat Temp., °C. | 79 | 79 | 79 | 79 |
| TDS Average Zonal Set Point Temps., °C. | | | | |
| Preheat | | | | |

TABLE VII-continued

Properties of Biaxially Stretched Microporous Sheets Produced from Precursor Sheet of Example 3

| Example No. | 22 | 23 | 24 | 25 |
|---|---|---|---|---|
| (lower banks) Stretch I | 177 | 149 | 177 | 177 |
| (lower banks) | 177 | 149 | 177 | 177 |
| Stretch II | 171 | 188 | 171 | 171 |
| Stretch III | 142 | 149 | 142 | 142 |
| Sinter I | 144 | 149 | 144 | 144 |
| Sinter II | 227 | 260 | 227 | 227 |
| Weight, g/m$^2$ | 27 | 14 | 20 | 14 |
| Porosity, vol % | 90 | 91 | 90 | 92 |
| Matrix Tensile Strength, MPa | | | | |
| MD | 29.58 | 52.94 | 77.84 | 109.89 |
| TD | 122.73 | 44.43 | 32.96 | 39.90 |
| Elongation at Break, % | | | | |
| MD | 90 | 47 | 27 | 17 |
| TD | 9 | 24 | 32 | 30 |
| Tear Strength, kN/m | | | | |
| MD | 15.41 | 10.51 | 15.24 | 7.18 |
| TD | 21.02 | 5.43 | 4.20 | 3.50 |
| Gurley Air Flow, sec/100 cc | 56 | 33 | | 36 |
| Mullens Hydrostatic, kPa | 552 | 655 | 641 | 586 |
| MVTR, g/m$^2$day | 843 | 815 | 862 | 982 |
| Methanol Bubble Point Pressure, kPa | 303 | 276 | | 317 |
| Maximum Limiting Pore Diameter, μm | 0.074 | 0.081 | | 0.070 |
| Heat Shrinkage after 1 hr at 100° C., % | | | | |
| MD | | 24.1 | 16.5 | 26.4 |
| TD | | 40.1 | 31.4 | 34.8 |

Precursor Sheet Formation

Larger batch mixing equipment was employed than was used for Examples 1–3. Processing oil was used as the processing plasticizer. Silica, polymer, lubricant, and antioxidant in the amounts specified in Table VIII were placed in a high intensity mixer and mixed at high speed for 6 minutes. The processing oil needed to formulate the batch was pumped into the mixer over a period of 12–18 minutes with high speed agitation. After completion of the processing oil addition a 6 minute high speed mix period was used to complete the distribution of the processing oil uniformly throughout the mixture.

TABLE VIII

| | Formulations | |
|---|---|---|
| Example | 26 | 27 |
| Ingredient | | |
| UHMWPE (1), kg | 24.04 | 17.24 |
| HDPE (2), kg | 0.00 | 6.80 |
| Precipitated Silica (3), kg | 59.87 | 59.87 |
| Lubricant (4), g | 300.0 | 300.0 |
| Antioxidant (5) g | 300.0 | 300.0 |
| Processing Oil (6), kg | | |
| in Batch | 91.63 | 91.63 |
| at Extruder | ~35.14 | ~35.14 |

(1) UHMWPE = Ultrahigh Molecular Weight Polyethylene, Himont 1900, Himont, U.S.A., Inc.
(2) HDPE = High Density Polyethylene, Chevron 9690T, Chevron Chemical Co.
(3) HiSil ® SBG, PPG Industries, Inc.
(4) Petrac ® CZ81, Desoto, Inc., Chemical Speciality Division
(5) Irganox ® B-215, Ciba-Geigy Corp.
(6) Shellflex ® 371, Shell Chemical Co.

The batch was then processed according to the general procedures described in respect of Examples 1–3 to form precursor microporous sheets.

The precursor microporous sheets, as well as the hereinafter described biaxially stretched microporous sheets produced therefrom, were tested for various physical properties. Table II identifies the properties with the methods used for their determination. The results of physical testing of the precursor microporous sheets are shown in Table IX. The abbreviations MD and TD have the same meanings previously discussed.

TABLE IX

| Physical Properties of Precursor Microporous Sheet | | |
|---|---|---|
| Example No. | 26 | 27 |
| Ingredient | | |
| Thickness, mm | 0.267 | 0.254 |
| Strip Tensile Strength, kN/m | | |
| MD | 3.42 | |
| TD | 1.52 | |
| Breaking Factor, kN/m | | |
| MD | | 3.44 |
| TD | | 1.42 |
| Elongation at break, % | | |
| MD | 391 | 477 |
| TD | 448 | 451 |
| Processing Oil Content, wt % | 2.8 | 3.3 |

Biaxial Stretching of Precursor Microporous Sheet

Portions of the precursor microporous materials produced in Examples 26 and 27 were unwound from cores and biaxially stretched by first uniaxially stretching in the machine direction using a single stage roll-to-roll MDS unit and then essentially uniaxially stretching in the transverse direction using a moving clip tenter frame as a TDS unit. Operation of the MDS unit can be characterized by the temperatures and line speeds shown in Table X.

TABLE X

| | MDS Unit Parameters | | | |
|---|---|---|---|---|
| Roll No. | Function | Diameter, mm | Temperature, °C. | Peripheral Speed, m/min |
| 1 | Preheat | 305 | 116 | 3.84 |
| 2 | Preheat | 305 | 116 | 3.84 |
| 3 | Stretching | 152 | 127 | 3.84 |
| 4 | Stretching | 152 | 127 | 11.52 |
| 5 | Annealing | 305 | 79 | 11.53 |
| 6 | Cooling | 305 | 38 | 11.53 |

The gap between the slow and fast stretching rolls (Rolls 3 and 4, respectively) was 0.533 millimeter. The TDS unit was a typical chain and clip tentering frame machine. It comprised three contiguous heating zones, each 2.54 meters in length where the beginning of the first heating zone coincided with the entrance to the TDS unit. The microporous sheet was heated by recirculating hot air in the heating zones. The heating zone temperatures are indicated in Table XI, where heating zone numbers increase in the direction of sheet travel.

TABLE XI

| Heating Zone Temperature | |
|---|---|
| Heating Zone | Temperature, °C. |
| 1 | 107 |
| 2 | 116 |
| 3 | 121 |

Stretching was controlled by positioning the tracks in which the chains holding the gripping clips rode. Microporous sheets, which had been uniaxially stretched in the machine direction as described above, were introduced to the TDS unit which had the track geometry shown in Table XII.

TABLE XII

| Track Geometry of TDS Unit | |
|---|---|
| Distance from Entrance, meters | Width, meters |
| −0.30 | 0.53 |
| +1.22 | 0.53 |
| 2.01 | 0.53 |
| 2.74 | 0.74 |
| 3.51 | 0.97 |
| 4.27 | 1.17 |
| 5.03 | 1.38 |
| 5.79 | 1.60 |
| 7.32 | 1.60 |
| 7.92 | 1.57 |

The properties of representative samples of biaxially stretched microporous sheets are given in Table XIII.

TABLE XIII

| Properties of Biaxially Stretched Microporous Sheets | | |
|---|---|---|
| Example No. | 28 | 29 |
| Microporous Sheet Feedstock, Example No. | 26 | 27 |
| Thickness, mm | 0.228 | 0.250 |
| Stretch Ratio | | |
| MD | 3 | 3 |
| TD | 3 | 3 |
| Line Speed, m/min | 13.4 | 13.4 |
| Weight, g/m$^2$ | 19.67 | 21.56 |
| Porosity, vol % | 92.1 | 91.1 |
| Strip Tensile Strength, kN/m | | |
| MD | 1.175 | 1.158 |
| TD | 0.716 | 0.412 |
| Elongation at break, % | | |
| MD | 41 | 39 |
| TD | 54 | 61 |
| Gurley Air Flow, sec/100 cc | 41 | 48 |
| Mullens Hydrostatic, kPa | 600 | 579 |

EXAMPLE 30

A portion of the biaxially stretched microporous sheet of Example 9 was cut into two rectangles each measuring approximately 21½ centimeters by 23 centimeters. The rectangles of microporous material were superimposed to form two plies and used to make an artificial carnation according to the procedure commonly used for making artificial carnations from ordinary facial tissues. To this end, the superimposed rectangles of microporous material were folded accordion-style into pleats approximately 1¾ centimeters wide with the folds running parallel to the 23 centimeter dimension. With the pleats pressed into their folded positions, the folded structure which had a length of about 23 centimeters and a width of about 1¾ centimeters was folded onto itself in the middle so that the length of the resulting folded assembly was about 11½ centimeters and the width was about 1¾ centimeters. Soft copper wire having a diameter of about 1 millimeter and a length of about 28 centimeters was bent approximately in the middle into the shape of a narrow "U". The folded assembly was placed between the arms of the bent wire such that the bend in the wire was in contact with the middle of the thickness dimension of the folded assembly and the arms of the wire were approximately perpendicular to the thickness dimension. While compressing the portion of the folded assembly near the arms of the wire toward the bend in the wire, the arms of the wire were tightly twisted for a few turns near the folded assembly to securely hold the folded assembly in place. The remaining lengths of the two arms were then lightly twisted throughout their length to form an artificial stem. The bend resulting from folding the folded structure on itself was cut through with scissors. The accordion folds near the free ends were expanded somewhat so that the periphery of the folded assembly assumed a generally circular shape. The two plies of microporous material were then separated at and near the free ends of the folded assembly and gently pulled in opposite directions along the periphery so that the accordion folds were no longer superimposed at and near the free ends. The microporous material was then shaped into the form of a carnation by pulling downward on the artificial stem while pressing upward on the microporous material near and around the artificial stem. The resulting base of the artificial carnation was wrapped with green florist's tape to retain the shape of the base and to form a pseudo-calyx. The artificial stem was also wrapped with green florist's tape to cover the twisted wires and provide a more nearly authentic color. The free ends and unwrapped portions of the microporous material constituted the artificial petals. Upon minor readjustment and fluffing of the artificial petals according to individual preference, the artificial carnation was complete.

EXAMPLE 31

A first solution was prepared by dissolving about 15 cubic centimeters of No. 7 Rose Pink RIT ® dye (CPC International, Inc.) in about 600 milliliters of water.

A second solution was prepared by adding 40 drops of No. 4001 Rose Petal fragrance (Chemia Corp.). and 20 drops of No. 3008 Rose fragrance (Chemia Corp.) to about 400 milliliters of absolute ethanol.

A dying and perfuming solution was prepared by admixing all of the first and second solutions.

A portion of biaxially stretched microporous sheet produced in accordance with the principles heretofore described was immersed in the above dying and perfuming solution at room temperature until the microporous material was dyed a light pink color. The dyed and perfumed microporous material was then removed from the dying and perfuming solution and allowed to dry. During immersion and/or drying, the microporous material shrunk slightly. The dry microporous material was gently stretched by hand both in the machine direction and in the transverse direction, but not so much as to restore it to the original dimensions.

A PRETTY PETALS ® No. 3R-30 Silky Sweetheart Rose artificial flower kit (Signaigo & Rossi, Inc., d.b.a. Sirocraft) was purchased. One of the tetrapetalous No. 3R rose cuts from the kit was used as a pattern from which a die was fabricated. The die was used to cut three identical tetrapetalous artificial petal elements from the above dyed and perfumed microporous material and a small hole was punched in the center of each. The artificial petals of each artificial petal element were stretched slightly over a large ball bearing to provide the gentle dish-shaped appearance characteristic of true rose petals. One of the artificial petal elements is shown diagrammatically in FIG. 1 where artificial petal element 10 comprises petals 12 and central coalescence 14 having hole 16 centrally located. The artificial petals 12 are separated by sinuses 18. The tips of opposing petals were about 7.8 centimeters apart while the innermost points of opposing sinuses were about 1.8 centimeters apart.

Figure 2:
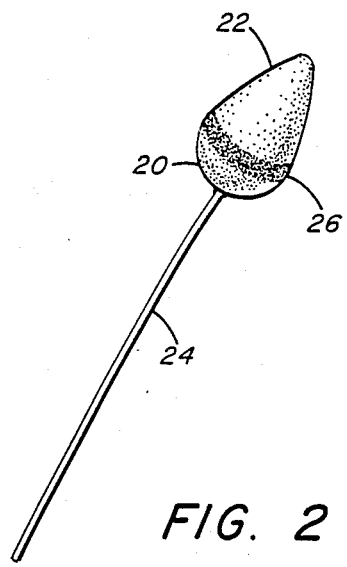
FIG. 2 shows diagrammatically a mold.

FIG. 2 shows diagrammatically a No. 717 white cotton mold from the kit. The mold 20 comprised generally teardrop-shaped mold head 22 formed of cotton wrapped about wire 24. The cotton was sized to increase firmness and to hold the cotton in place. Equator 26 is a narrow region encircling the surface of mold head 22 at its largest cross-section perpendicular to the axis of symmetry. The diameter of equator 26 was about 1.6 centimeters while the length of mold head 22 along the axis of symmetry was about 2.0 centimeters. A band of white glue was placed on mold head 22 along equator 26.

Figure 3:
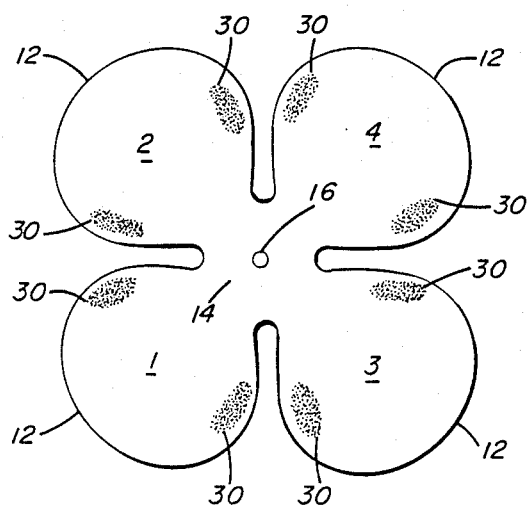
FIG. 3 shows diagrammatically an artificial petal element.

FIG. 3 shows diagrammatically one of the artificial petal elements described with reference to FIG. 1. White glue was placed locally on both lateral regions 30 of the slightly concave sides of each of artificial petals 12 of this first artificial petal element. With the glue on artificial petals 12 facing upwardly, wire 24 of mold 20 (FIG. 2) was inserted downwardly through hole 16 until coalescence 14 touched the bottom of mold head 22. Artificial petals 12 were then wrapped around mold head 22 in the order 1, 2, 3, 4 and held until the glue along equator 26 and on lateral regions 30 had dried at least sufficiently to hold the artificial petals in place. The lateral extremities of the first artificial petal when in place on mold head 22 did not quite overlap while the portions near the tip substantially sheathed the upper portion of mold head 22. The portions near the tips of the other three artificial petals were progressively less enveloping of the upper portion of mold head 22 in accordance with the order in which they were positioned.

Figure 4:
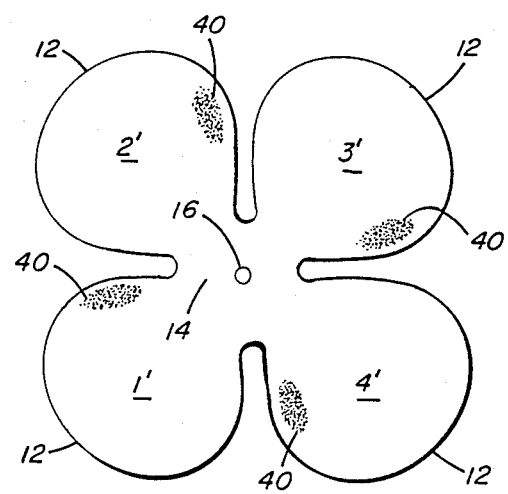
FIG. 4 shows diagrammatically another artificial petal element.

FIG. 4 shows diagrammatically another of the artificial petal elements described with reference to FIG. 1. White glue was placed locally on only one lateral region 40 of the slightly concave sides of each of artificial petals 12 of this second artificial petal element. With the glue on artificial petals 12 facing upwardly, wire 24 of mold 20 was inserted downwardly through hole 16 until coalescence 14 of the second artificial petal element touched the coalescence 14 of the previously positioned first artificial petal element. The second petal element was rotated until the axes of symmetry through opposing sinuses was at about 45 degrees from the corresponding axes of symmetry of the first artificial petal element. In the order 1', 2', 3', 4', artificial petals 12 of the second artificial petal element were then wrapped around the previously positioned artificial petals 12 of the first artificial petal element and held until the glue on lateral regions 40 had dried at least sufficiently to hold the newly positioned artificial petals in place.

White glue was applied to the artificial petals of a third artificial petal element and the artificial petals were wrapped around the previously positioned artificial petals of the second artificial petal element, all in a manner analogous to that of the second artificial petal element, including the 45 degree rotational offset.

Figure 5:
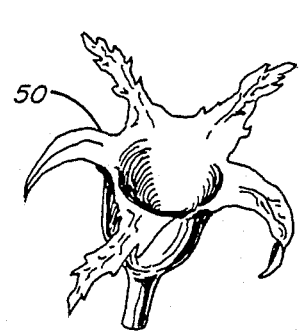
FIG. 5 shows diagrammatically an artificial calyx.

FIG. 5 shows diagrammatically a No. P-200B artificial plastic calyx 50 from the kit. White glue was placed on the edge of artificial calyx 50 and wire 24 (FIG. 2) was inserted into the central hole (not shown) of artificial calyx 50. Artificial calyx 50 was then pushed up wire 24 until it enveloped coalescence 14 (FIG. 4) of the previously positioned third petal element. The glue was allowed to dry.

Figure 6:
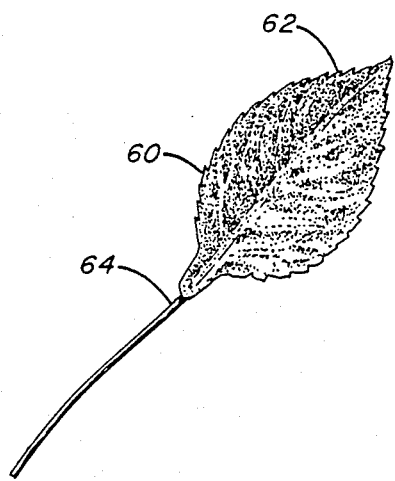
FIG. 6 shows diagrammatically an artificial leaf.

FIG. 6 shows diagrammatically a J740s artificial leaf 60 from the kit. Artificial leaf 60 comprises artificial blade 62 of sized green fabric which is glued to green paper-covered wire 64. The portion of covered wire 64 in contact with artificial blade 62 functions as an artificial midrib while the remainder functions as an artificial petiole. Artificial leaf 60 was placed such that the artificial petiole portion of covered wire 64 was parallel to and in contact with wire 24 and such that the lower portion of artificial blade 62 was in contact with the lower portion of artificial calyx 50. The lower portion of artificial calyx 50, the artificial petiole portion of covered wire 64, and wire 24 were wrapped together in helical fashion with green florist's tape, beginning at the lower portion of artificial calyx 50 and continuing past the lower end of covered wire 64 to the lower end of wire 24, to form an artificial stem.

Figure 7:
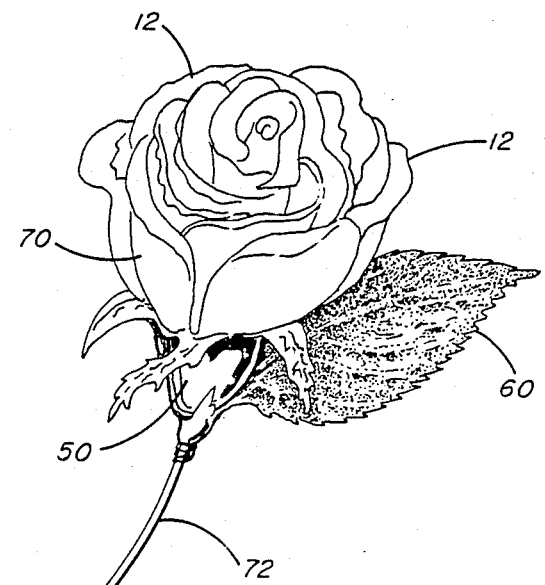
FIG. 7 shows diagrammatically a completed embodiment of the invention.

The tips of some of the artificial petals were bent back slightly into a recurved position. Upon minor adjustment of the artificial petals according to individual preference, the artificial rose was complete. FIG. 7 shows diagrammatically the completed artificial rose 70, comprising artificial petals 12, artificial calyx 50, artificial leaf 50, and artificial stem 72.

Although the present invention has been described with reference to specific details of certain embodiments thereof, it is not intended that such details should be regarded as limitations upon the scope of the invention except insofar as they are included in the accompanying claims.

What is claimed is:

1. In an artificial flower comprising at least one artificial petal, the improvement wherein said artificial petal comprises microporous material which comprises:
   (a) a matrix consisting essentially of essentially linear ultrahigh molecular weight polyolefin which is essentially linear ultrahigh molecular weight polyethylene having an intrinsic viscosity of at least about 18 deciliters/gram, essentially linear ultrahigh molecular weight polypropylene having an intrinsic viscosity of at least about 6 deciliters/gram, or a mixture thereof; said matrix comprising regions of stretch-induced molecularly oriented ultrahigh molecular weight polyolefin distributed throughout said matrix,
   (b) finely divided particulate substantially water-insoluble siliceous filler distributed throughout said matrix, said filler constituting from about 50 percent to about 90 percent by weight of said microporous material, and
   (c) a network of interconnecting pores communicating throughout said microporous material, said pores constituting more than 80 percent by volume of said microporous material.

2. The artificial flower of claim 1 wherein said essentially linear ultrahigh molecular weight polyolefin is essentially linear ultrahigh molecular weight polyethylene having an intrinsic viscosity of at least about 18 deciliters/gram.

3. The artificial flower of claim 2 wherein high density polyethylene is present in said matrix.

4. The artificial flower of claim 2 wherein said ultrahigh molecular weight polyethylene has an intrinsic viscosity in the range of from about 18 to about 39 deciliters/gram.

5. The artificial flower of claim 2 wherein said filler constitutes from about 50 percent to about 85 percent by weight of said microporous material.

6. The artificial flower of claim 2 wherein said filler is silica.

7. The artificial flower of claim 2 wherein said inorganic filler is precipitated silica.

8. The artificial flower of claim 7 wherein said precipitated silica has an average ultimate particle size of less than about 0.1 micrometer.

9. The artificial flower of claim 2 wherein the volume average diameter of said pores as determined by mercury porosimetry is in the range of from about 0.6 to about 50 micrometers.

10. The artificial flower of claim 2 wherein said pores constitute from about 85 percent to about 95 percent by volume of said microporous material.

11. The artificial flower of claim 2 wherein said microporous material has a thickness in the range of from about 0.03 to about 0.25 millimeter.

12. The artificial flower of claim 11 which exhibits high degrees of suppleness and softness to the touch.

13. The artificial flower of claim 12 wherein all artificial petals of said artificial flower are of said microporous material.

14. The artificial flower of claim 2 wherein said petal contains colorant.

15. The artificial flower of claim 2 wherein said petal contains perfume.

16. The artificial flower of claim 1 wherein said petal contains colorant.

17. The artificial flower of claim 1 wherein said petal contains perfume.

18. The artificial flower of claim 1 wherein said petal has been printed.

19. An artificial flower comprising at least one artificial petal of microporous material exhibiting high degrees of suppleness and softness to the touch and having a thickness in the range of from about 0.03 to about 0.25 millimeter, said microporous material comprising:

(a) a matrix consisting essentially of essentially linear ultrahigh molecular weight polyethylene having an intrinsic viscosity of at least about 18 deciliters/gram, said matrix comprising regions of stretch-induced molecularly oriented ultrahigh molecular weight polyethylene distributed throughout said matrix, (b) finely divided particlulate precipitated silica having an average ultimate particle size of less than about 0.1 micrometer distributed throughout said matrix, said precipitated silica constituting from about 50 to about 90 percent by weight of said microporous material, and (c) a network of interconnecting pores having a volume average diameter as determined by mercury porosimetry in the range of from about 0.6 to about 50 micrometers communicating throughout said microporous material, said pores constituting more than 80 percent by volume of said microporous material.

20. The artificial flower of claim 19 wherein said petal contains colorant.

21. The artificial flower of claim 19 wherein said petal contains perfume.

22. The artificial flower of claim 1 which is an artificial carnation comprising petals of said microporous material.

23. The artificial flower of claim 22 wherein said petals contain colorant.

24. The artificial flower of claim 22 wherein said petals contain perfume.

25. The artificial flower of claim 1 which is an artificial rose comprising petals of said microporous material.

26. The artificial flower of claim 25 wherein said petals contain colorant.

27. The artificial flower of claim 25 wherein said petals contain perfume.

* * * * *